United States Patent
MacDonald et al.

(10) Patent No.: US 9,265,891 B2
(45) Date of Patent: Feb. 23, 2016

(54) ASSEMBLY OF A DRUG DELIVERY DEVICE

(75) Inventors: Catherine Anne MacDonald, Ashby-de-la-Zouch (GB); Robert Veasey, Leamington Spa (GB); Garen Kouyoumjian, Leamington Spa (GB); Christopher Jones, Tewkesbury (GB); Andrew Mark Lindsay, Hinckley (GB); Michael Bainton, Kineton (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 243 days.

(21) Appl. No.: 13/395,840

(22) PCT Filed: Sep. 29, 2010

(86) PCT No.: PCT/EP2010/064404
§ 371 (c)(1),
(2), (4) Date: Jul. 31, 2012

(87) PCT Pub. No.: WO2011/039213
PCT Pub. Date: Apr. 7, 2011

(65) Prior Publication Data
US 2012/0302964 A1    Nov. 29, 2012

(30) Foreign Application Priority Data

Sep. 30, 2009   (EP) ..................... 09171746

(51) Int. Cl.
*A61M 5/00* (2006.01)
*A61M 5/315* (2006.01)
*A61M 5/20* (2006.01)

(52) U.S. Cl.
CPC ..... *A61M 5/3155* (2013.01); *A61M 2005/2073* (2013.01)

(58) Field of Classification Search
CPC ................. A61M 1/3643; A61M 2005/1402;
A61M 5/2033; A61M 5/30; A61M 5/24;
A61M 2205/581; A61M 5/31593; A61M
5/31553; A61M 5/3158; A61M 5/31541;
A61M 5/31585; A61M 2005/2013; A61M
5/31551; A61M 5/31578; A61M 5/31
USPC .............. 604/82–92, 191, 198, 207–211, 220
See application file for complete search history.

(56) References Cited

U.S. PATENT DOCUMENTS 4,710,178 A * 12/1987 Henri et al. .................... 604/209
5,092,842 A *  3/1992 Bechtold et al. ............... 604/135
(Continued)

FOREIGN PATENT DOCUMENTS

EP      0409365 A1    1/1991
EP      0450905 A1   10/1991
(Continued)

OTHER PUBLICATIONS

Form PCT/IB/409, International Preliminary Report on Patentability, Mar. 16, 2010.

*Primary Examiner* — Scott Medway
(74) *Attorney, Agent, or Firm* — McDonnell Boehnen Hulbert & Berghoff LLP (57) ABSTRACT

An assembly of a drug delivery device with a longitudinal axis (L) is given, comprising a body (1) with a proximal end (2) and a distal end (3). The drug delivery device further comprises a drive assembly and a first button member (4). The drive assembly is at least partially arranged within the body (1) and is adapted to facilitate dispense of a medicinal product. The first button member (4) acts on the drive assembly to prepare the drug delivery device for dispensing the medicinal product. The first button member (4) is adapted to be detachable from the body (1) after the preparation of the drug delivery device is completed.

15 Claims, 2 Drawing Sheets

(56) References Cited

U.S. PATENT DOCUMENTS

| | | | | |
|---|---|---|---|---|
| 5,112,317 | A * | 5/1992 | Michel | 604/208 |
| 5,514,097 | A * | 5/1996 | Knauer | 604/136 |
| 6,059,755 | A * | 5/2000 | Michel | 604/207 |
| 6,210,369 | B1 * | 4/2001 | Wilmot et al. | 604/157 |
| 6,610,028 | B1 * | 8/2003 | Alexandre et al. | 604/69 |
| 6,656,163 | B1 * | 12/2003 | Marshall et al. | 604/198 |
| 2004/0186442 | A1 * | 9/2004 | Graf et al. | 604/207 |
| 2005/0137534 | A1 * | 6/2005 | Hommann | 604/224 |
| 2005/0261634 | A1 * | 11/2005 | Karlsson | 604/197 |
| 2006/0167412 | A1 * | 7/2006 | Marshall | 604/110 |
| 2007/0233015 | A1 * | 10/2007 | Saiki | 604/207 |
| 2008/0154211 | A1 * | 6/2008 | Moller | 604/211 |
| 2008/0287920 | A1 * | 11/2008 | Fangrow et al. | 604/535 |
| 2010/0010454 | A1 * | 1/2010 | Marshall et al. | 604/208 |
| 2010/0160894 | A1 * | 6/2010 | Julian et al. | 604/506 |
| 2011/0046565 | A1 * | 2/2011 | Radmer et al. | 604/211 |
| 2012/0165744 | A1 * | 6/2012 | Jones | 604/189 |
| 2012/0265136 | A1 * | 10/2012 | Lawlis et al. | 604/110 |
| 2014/0354998 | A1 * | 12/2014 | Bock et al. | 356/445 |

FOREIGN PATENT DOCUMENTS

| | | |
|---|---|---|
| EP | 0702971 A2 | 3/1996 |
| WO | 9710865 A1 | 3/1997 |
| WO | 9930759 A2 | 6/1999 |

* cited by examiner

ASSEMBLY OF A DRUG DELIVERY DEVICE

CROSS REFERENCE TO RELATED APPLICATIONS

The present application is a 35 U.S.C. 371 National Application of PCT/EP2010/064404 filed Sep. 29, 2010, which claims priority to European Patent Application No. 09171746.2, filed Sep. 30, 2009, the entire contents of which are incorporated entirely herein by reference.

The present invention relates to an assembly of a drug delivery device.

Drug delivery devices are generally known for the administration of a medicinal product, such as for example heparin, insulin or human growth hormones. The medicinal product may be self administered by a patient.

Before administering the first dose of the medicinal product, the drug delivery device and the assembly of such device, respectively, must be prepared correctly. A patient, who is unfamiliar with such preparation, may fail or incorrectly prepare the device before dispensing and administering the first dose. Further, as the drug delivery device may be used on an irregular basis, a patient may forget or become confused about whether or not the drug delivery device has already been prepared.

It is an object to the present disclosure to provide an assembly of a drug delivery device, which helps to ensure that a user correctly prepares the drug delivery device and so improves the accuracy of the first dispensed dose of a medicinal product making the administration of a medicinal product safer and more effective.

Independent claims 1 and 4 meet this requirement. Aspects and several embodiments are subject to the dependent claims.

The term "assembly of a drug delivery device" corresponds to the term drug delivery device.

The term "medicinal product" or "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

An assembly of a drug delivery device with a longitudinal axis according to the invention may comprise a body with a proximal end and a distal end. The assembly further may comprise a drive assembly being at least partially arranged within the body. The drive assembly is adapted to facilitate dispense of a medicinal product. The assembly may additionally comprise a first button member which acts on the drive assembly to prepare the drug delivery device for dispensing the medicinal product. The first button member is adapted to be detachable from the body after the preparation of the drug delivery device is completed.

The drug delivery device is a device of any shape, for example the device might be compact or pen-shaped. The device may deliver a single dose or multiple doses of a medicinal product. The dose can be pre-set, pre-defined or selectable. The drug delivery device can be disposable or reusable. Furthermore, the said drug delivery device may comprise a needle or may be needle-free. An attached needle can be fixed or replaceable.

The body may be an exterior structure, as for example a main body portion or an outer shell of the assembly of the drug delivery device, or an interior structure. The body may be designed to enable the safe, correct and comfortable handling of the assembly of the drug delivery device and/or any of its mechanism. It may be designed to house, protect or guide components of the drug delivery device. The body may additionally engage with any of the inner components of the assembly of the drug delivery device, as for example the drive assembly, a drive mechanism, a cartridge, a plunger, a piston rod or lead screw. The body may be a single or a multipart component. The body may be of a tubular or non-tubular shape. The body may serve to house a cartridge from which a number of doses of a medicinal product may be dispensed. The body may comprise a cartridge holder.

The body helps to limit the exposure of internal components to contaminants, such as liquid, dirt or dust. The cartridge holder may serve to house the cartridge which might be replaceable or non-replaceable. A number of doses of a medicinal product may be dispensed from a cartridge.

The term facilitating dispense of a medicinal product implies any procedure undertaken on the drug delivery device, resulting in a delivery of the medicinal product, including, but not limited thereto, setting up a dose of a medicinal product and dispensing the dose.

A drive assembly may be arranged substantially within the body to facilitate dispense of a medicinal product. The drive assembly may comprise one or more different parts, which are partially arranged within the body and partially outside the body. Preferably, parts of the drive assembly, which are arranged outside the body, are arranged outside the proximal end of the body. Different mechanical parts of the drive assembly may act upon each other to facilitate dispense of the medicinal product. In this respect, the drive assembly may be adapted to set up a dose of the medicinal product to be delivered and to dispense this dose in a subsequent step.

The drive assembly may comprise at least one moving portion or one drive sleeve. The term moving portion may be an element which is restricted to an axial and/or rotational and/or helical movement within the body for driving the piston rod. The term drive sleeve implies an element which may be arranged between the button and the piston rod. The term drive sleeve may additionally imply an element comprising a helically shaped surface, that surface being in operative connection with, for instance, the body, the piston rod, a lead screw or any other part of the drive assembly. In an embodiment, the drive sleeve may comprise a helically shaped surface which engages a piston rod. In yet another embodiment, the drive sleeve may comprise a helically shaped surface that engages a lead screw nut which may be rigidly fixed to the body of the drug delivery device or integrated into the body.

The drive assembly may comprise a piston rod, arranged at least partly within the body and axially displaceable towards the distal end of the body. The piston rod may comprise some teeth which act upon other parts of the drive assembly, thereby allowing displacement of the piston rod towards the distal end. The piston rod may additionally comprise a thread form or helical guide track which causes it to perform a twist movement in order to be displaced towards the distal end. Accordingly, the drive assembly may comprise an element which is rotated or screwed to axially move towards the distal end.

The piston rod is a part of the assembly of the drug delivery device adapted to operate at least partially within the body. The piston rod may be designed to translate axial movements from a drive sleeve to a piston. The piston rod may be flexible or not. It may be, but is not limited thereto, a simple rod, a lead-screw, a rack and pinion system, a worm gear system. The piston rod may have a circular or non-circular cross-section. It may be a single or multipart component. It may comprise one or more sets of longitudinal spaced ribs and/or indentations or the like. The piston rod may push a bung of the cartridge along the inside wall of the cartridge during drug delivery, thereby delivering the drug.

The first button member may be adapted to axially displace the piston rod of the drive assembly with respect to the body to prepare the drug delivery device.

In this respect, the pre-ready state implies a state of the assembly of the drug delivery device, in which the drug delivery device is unprepared for facilitating dispense of a medicinal product. In other words, the drug delivery device has still to be prepared for dispensing a medicinal product. During preparation the assembly of the drug delivery device for facilitating dispense of the medicinal product and particularly facilitating the deliberate and desired dispense of a medicinal product, the assembly of the drug delivery device is in the transient state. The transient state chronologically follows the pre-ready state and is chronologically ahead the ready state. The ready state may directly follow the transient state.

The term "prepare" implies any operation upon the drug delivery device which prepares the drug delivery device for later dispense of a desired amount of medicinal product. This may include, but is not restricted thereto, priming the drug delivery device including compensating for any backlashes and tolerances of mechanical parts of the drive assembly and the drug delivery device, closing a gap between the bung and the drive assembly, mixing powder with a fluid to generate the medicinal product and/or expelling a priming portion of the medicinal product or air.

Priming the drug delivery device may imply that the parts of the driving mechanism are moved to their predetermined position with respect to the other parts to dispense the predetermined dose of the medicinal product. The priming makes the assembly of the drug delivery device ready for use. Priming the drug delivery device is useful for the dose accuracy and for flushing a needle which might be fitted to an assembled cartridge. Therefore, it is useful to draw the attention of the user to the need to prime the drug delivery device and to force the user to prime the drug delivery device through a recognizably different action before dose setting and dose dispensing actions are enabled.

The assembly of the drug delivery device or parts of it may be disposable or reusable. When the drug delivery device is assembled or parts of the drug delivery device, e.g. the cartridge, are exchanged, the parts of the driving mechanism may be not positioned in a predetermined position with respect to the cartridge or the body of the drug delivery device. If the parts are positioned in the predetermined position, this ensures that a predetermined dose is delivered when the drug delivery device is used the first time after assembling. After assembly there may be an internal gap between parts of the drug delivery device which have to contact each other to ensure the delivery of the correct dose of medicament. The gap may be located between parts of the drive assembly or between a part of the drive assembly and e.g. the cartridge. The gap is a consequence of tolerances associated with all the assembled parts.

The axial displacement of the piston rod may imply a movement of the piston rod in parallel to the longitudinal axis.

In this respect, a rotational movement may imply a rotation of a part of the assembly of the drug delivery device around the longitudinal axis right-angled to the longitudinal axis.

The distal end of the body is an end of the body which is closest to the dispensing end of the drug delivery device.

The proximal end of the body is the end of the body which is furthest away from the dispensing end of the drug delivery device.

The first button member is a member of the assembly which might be located at the proximal end of the body. The first button member may be a button. The user operates the first button member to prepare the drug delivery device during the pre-ready state. The first button member may be moveable relative to the body of the assembly of the drug delivery device. The operation of the first button member by the user may include, but is not limited thereto, a twist operation, a rotation of the first button member, a movement of the first button member parallel to the longitudinal axis of the drug delivery device, pushing or pulling of the first button member.

The first button member may be adapted to be irreversibly detachable from the body, in particular after the preparation of the drug delivery device is completed. The term "irreversibly detachable" may imply a feature of the assembly of the drug delivery device which contributes to preventing an attachment of the first button member to the body after the preparation of the drug delivery device is completed. The term "irreversibly detachable" may additionally imply a blocking feature which basically blocks the first button member from attaching to the assembly of the drug delivery device after the first button member is detached from the body of the assembly of the drug delivery device.

The assembly may comprise a second button member which acts on the drive assembly to dispense the medicinal product. The second button member is inaccessible as long as the preparation of the drug delivery device is uncompleted.

The second button member may be adapted to axially displace the piston rod of the drive assembly with respect to the body to dispense the medicinal product.

The term "uncompleted preparation" implies that the drug delivery device is in the pre-ready or transient state, in which the drug delivery device respectively the assembly of such a device is before the first use for dispensing for example a predetermined dose of the medicinal product. If the drug delivery device is in the pre-ready state, the user has to prepare the device before the user is enabled to set and dispense the predetermined dose of the medicinal product. The preparation renders the drug delivery device and respectively the assembly of the drug delivery device ready for use.

According to another aspect of the invention an assembly of a drug delivery device with a longitudinal axis may comprise a body with a proximal end and a distal end. The assembly may further comprise a drive assembly being at least partially arranged within the body. The drive assembly is adapted to facilitate dispense of a medicinal product. The assembly may additionally comprise a first button member which acts on the drive assembly to prepare the drug delivery device for dispensing the medicinal product. The assembly may further comprise a second button member which acts on the drive assembly to dispense the medicinal product. The second button member is inaccessible as long as the preparation of the drug delivery device is uncompleted.

The second button member is a member of the assembly of the drug delivery which might be located at the proximal end of the body. The second button member may be a button. The user operates the second button member to dispense the medicinal product. The second button member may be adapted to axially displace the piston rod with respect to the body to dispense the medicinal product in the ready state. The second button member may be moveable relative to the body of the assembly of the drug delivery device. The operation of the second button member by the user may include, but is not limited thereto, a twist operation, a rotation of the second button member, a movement of the second button member parallel to the longitudinal axis of the drug delivery device, pushing or pulling of the second button member.

The second button member is inaccessible as long as the assembly is in its pre-ready or transient state, i.e. as long as the preparation of the drug delivery device is uncompleted. The second button member can be rendered inaccessible by for example at least partially encasing it by the first button member as long as the preparation of the drug delivery device is uncompleted. The term "inaccessible" may additionally imply that the second button member is non-functional when the assembly of the drug delivery device is in the pre-ready or transient state. This may be realized by operationally decoupling the second button member from the drive sleeve and/or the operation of the piston rod while the assembly of the drug delivery device is in the pre-ready or transient state. Furthermore, the first button member may be become non-functional when the assembly of the drug delivery device is in the ready state. This may be realized by operationally decoupling the first button member from the drive sleeve and/or the operation of the piston rod while the assembly of the drug delivery device is in the ready state.

The first button member may be adapted to be actuated in a predetermined movement to prepare the drug delivery device. The term "predetermined movement" may imply a movement of the first button member required to prepare the drug delivery device. The preparation may occur while moving the first button member according to the predetermined movement. The preparation may additionally be triggered after completing the predetermined movement of the first button member. The predetermined movement may comprise some helical movements or some axial and/or some twisting movements and/or some rotational movements of the first button member with respect to the body. After completing the preparation of the drug delivery device by moving the first button member according to the predetermined movement of the first button member, the first button member is detachable from the body of the assembly of the drug delivery device. The assembly of the drug delivery device may additionally comprise a detent feature to prevent re-attachment of the first button member after it has been detached. By this, a dispensing of a predetermined dose is essentially prevented as long as the preparation of the drug delivery device is uncompleted, i.e. as long as the assembly of the drug delivery device is in the pre-ready or transient state.

The body respectively the first button member of the assembly of the drug delivery device may additionally comprise at least one lug. The first button member or the body, respectively, may comprise at least one guiding track in which the at least one lug is guided. The guiding track predetermines the movement of the first button member with respect to the body to prepare the drug delivery device.

The lug may be an element that for example couples the first button member to the body of the assembly of the drug delivery device in the pre-ready state. The lug may be, but is not limited thereto, a projection or a rising on the first button member or on the body. The lug may be created while manufacturing the first button member or respectively the body.

The guiding track is a complementary element to the lug. The guiding track may be a first guiding recess being operable to at least partially encase the lug for example if the drug delivery device is in the pre-ready or transient state. The guiding track is adapted to guide the first button member with respect to the body according to the predetermined movement. The guiding track may be, but is not limited thereto, an elongate boring in the first button member or respectively the body and/or a recess and/or a channel within the first button member or respectively the body. The guiding track may comprise a helical shape, a lock, an edge, a recess, a projection, a channel, or a combination thereof. The guiding track may comprise a perpendicular portion by which the lug is encased in particular in the pre-ready state and in particular in the beginning of the transient state. The perpendicular portion may run perpendicular to the longitudinal axis. The perpendicular portion is applicable to prevent an unintentional axial movement of the first button member for example towards the distal end of the assembly of the drug delivery device. The guiding track may additionally comprise an oblique portion in which the lug is guided during the transient state. The oblique portion may run obliquely with respect to the longitudinal axis to enable an axial movement of the first button member while rotating it. The oblique portion directly follows up the perpendicular portion of the guiding track. The first button member and/or the body may additionally comprise at least one removing track which is adapted to encase the lug after the preparation of the drug delivery device. The at least one removing track may run in parallel to the longitudinal axis. The removing track may run at the inner surface of the first button member and/or at the perimeter of the body. Each removing track may be associated with a particular oblique portion and may be separated from the associated oblique portion of the guiding track by a detent. If the lug is arranged at an end of the oblique portion of the guiding track, wherein that end is remote from the perpendicular portion, the lug may get over the detent by for example pulling or pushing the first button member in axial direction. Afterwards, the lug is guided in the removing track to facilitate a detachment of the first button member from the body of the assembly of the drug delivery device. The detent represents a resistance against movement during preparation of the drug delivery device and represents a blocking mechanism or detent feature for preventing or at least hindering a re-attachment of the first button member to the body after the first button member has been detached from the body.

The drive assembly of the assembly of the drug delivery device may comprise a piston rod which is at least partially arranged within the body. The piston rod may be axially or twistably displaceable with respect to the body. The drive assembly may additionally comprise a drive sleeve which is arranged within the body. The drive sleeve may be axially or rotationally or twistably displaceable with respect to the body and may be coupled to the piston rod. The drive sleeve may be further coupled to the first button member to prepare the drug delivery device. Alternatively the drive sleeve may be fixed to the second button member and the second button member may be coupled to the first button member to prepare the drug delivery device. In the pre-ready state the second button member may be in a dose-set position, in which the second button member is moveable towards the distal end of the body without a previous setting movement in a proximal direction.

The drive sleeve is a part of the assembly of the drug delivery device that might be electronically or mechanically driven to expel a medicinal product from the drug delivery device. The drive sleeve may be operationally coupled with the first button member. The drive sleeve may be rotatable and/or twistable. The movement of the drive sleeve is determined by the movement of the first button member during preparation of the drug delivery device.

The body and/or the first button member may comprise at least one indicator for indicating the predetermined movement of the first button member with respect to the body.

The at least one indicator may imply a signal for attracting the attention of a user of the drug delivery device. The at least one indicator could for example be arrows or other symbols and might be located on the body, drive sleeve and/or the first button member. The at least one indicator indicates the predetermined movement, for example indicates the required helical movement and/or rotation and/or axial movement direction with respect to the body required to prepare the drug delivery device.

The assembly of the drug delivery device may be adapted to prevent an actuation of the first button member after the preparation the drug delivery device has been completed and the drug delivery device is in the ready state.

The assembly of the drug delivery device may be adapted to prevent the actuation of the first button member in a reverse predetermined movement after the preparation the drug delivery device has been completed and the drug delivery device is in the ready state.

The term "prevention of an actuation of the first button member" may imply a detent feature for basically preventing for example rotational and/or axial movements of the first button member with respect to the body. Due to tolerances of the assembled parts of the assembly of the drug delivery device an actuation of the first button member at least a small distance is of course always possible. The term covers additionally an actuation of the first button member within the scope of these tolerances as long as no further preparation is executed. This contributes to preventing a further preparation operation of the drug delivery device. The term may additionally imply a detent feature to basically prevent for example rotational and/or axial movements with respect to the body according to the reverse predetermined movement after the preparation of the drug delivery device has been completed. Alternatively, the prevention of the actuation of the first button member may additionally comprise a decoupling of the first button member from the body, second button member or drive assembly of example the drive sleeve after the drug delivery device has been prepared. The decoupling may imply unblocked movements of the first button member without any operationally coupling to the body, second button member or drive assembly of the assembly of the drug delivery device after it has been prepared and is in the ready state.

The term "actuating the second button member" implies movements of the second button member to dispense the medicinal product as for example rotational and/or axial movements. The second button member is operable to be actuated after the first button member has been detached from the body of the assembly of the drug delivery device. This may imply additionally a detent feature which basically prevents the actuation of the second button member until the drug delivery device has been prepared.

In the following, the disclosure is described in further detail with reference to the drawings, wherein.

Some preferred embodiments of the assembly of a drug delivery device according to the present disclosure will now be discussed with reference to FIGS. 1, 2 and 3a to 3c. Identical reference numerals denote identical or comparable components.

Figure 1:
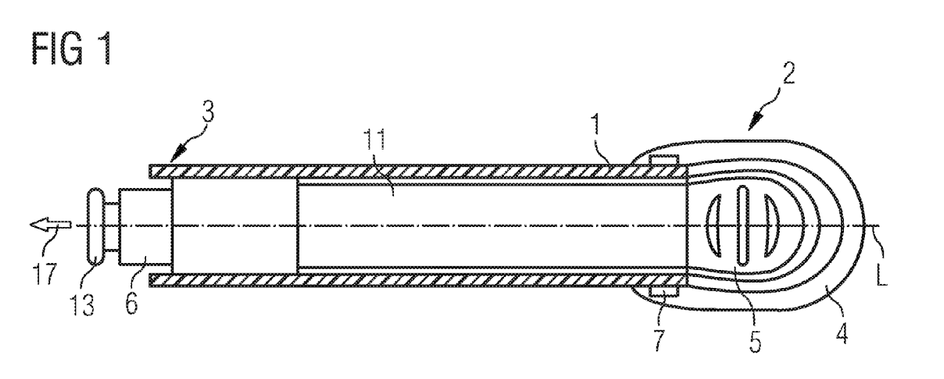
FIG. 1 shows a longitudinal section view for a drug delivery device.

FIG. 1 depicts an assembly of a pen-type drug delivery device in a longitudinal section view.

The assembly of the drug delivery device comprises a longitudinal axis L and a body 1 with a proximal end 2 and a distal end 3. A needle unit may be located at the distal end 3 of the body 1. Through a needle unit (not shown), a fluid medicinal product may be dispensed out of an assembled cartridge, which is not explicitly shown.

The assembly of a drug delivery device comprises additionally a cartridge holder, inside which a medicament cartridge is contained. The distal end 3 of the body 1 may serve as the cartridge holder. The body 1 comprises a drive sleeve 11 with a piston rod 6. The piston rod 6 comprises a bearing pad 13 which is for example adapted to be in contact with a bung of the cartridge. The drive sleeve 11 and the piston rod 6 with the bearing pad 13 represent a drive assembly of the assembly of the drug delivery device for facilitating to dispensing a medicinal product.

The assembly of the drug delivery device further comprises a first button member 4 which is located at the proximal end 2 of the body 1. The first button member 4 is for example a button and is adapted to prepare, for example prime, the drug delivery device. The first button member is further adapted to be detachable, in particular irreversibly detachable, from the body 1 after the drug delivery device has been prepared. The prepared drug delivery device corresponds to the ready state of the assembly of the drug delivery device. An uncompleted prepared drug delivery device corresponds to the pre-ready or transient state of the assembly of the drug delivery device.

The assembly of the drug delivery device may additionally comprise a second button member 5 as depicted in FIG. 1. The second button member 5 is located at the proximal end 2 of the body 1 and is for example a button. The second button member 5 is adapted to axially displace the piston rod 6 and the bearing pad 13 of the drive assembly with respect to the body 1 for dispensing a single dose or multiple doses of for example a fluid medicinal product.

The second button member 5 is inaccessible as long as the preparation of the drug delivery device is uncompleted. As shown in FIG. 1 the second button member 5 is fully encased by the first button member 4 to render it inaccessible as long as the first button member 4 is attached to the assembly of the drug delivery device. Alternatively, the second button member 5 is partially encased by the first button member 4. Other embodiments of the assembly of the drug delivery device to render the second button member 5 inaccessible as long as the preparation of the drug delivery device is uncompleted are additionally permissible.

The drive sleeve 11 is arranged within the body 1 and may be axially displaceable with respect to the body 1. Alternatively or additionally, the drive sleeve 11 is rotatable or twistable. In addition, the drive sleeve 11 is coupled to the piston rod 6 and thereby to the bearing pad 13.

The drive sleeve 11 of the assembly of the drug delivery device may additionally comprise a moving and a fixed portion (not shown) which are both in operative connection to each other. The moving portion is operationally coupled to the piston rod 6.

The first button member 4 may be adapted to be actuated in a predetermined movement to prepare the drug delivery device. The predetermined movement comprises some rotational and/or axial movements, wherein the rotational and axial movements can be combined to helical movement. This can be a pulling or pushing of the first button member 4 in combination with rotational movements. Additionally, twisting movements may be permissible in the predetermined movement. In this respect, the assembly of the drug delivery device is operable to basically prevent alternative movements of the first button member 4 to the predetermined movement. Alternatively, the assembly of the drug delivery device is operable to allow all kinds of possible movements of the first button member 4 but only prepare the drug delivery device if the first button member 4 is actuated in the predetermined movement. In this respect, the first button member 4 is only detachable after the predetermined movement is completed otherwise it stays attached to the assembly of the drug delivery device wherein the completed predetermined movement represents a completed preparation of the drug delivery device.

After completing the preparation of the drug delivery device the first button member 4 may be irreversibly detachable from the body 1. As indicated in FIG. 1 after detaching the first button member 4 the second button member 5 is accessible.

The second button member 5 is adapted to axially displace the piston rod 6 with respect to the body 1 to dispense a single dose or multiple doses of the medicinal product after the drug delivery device has been prepared.

Figure 2:
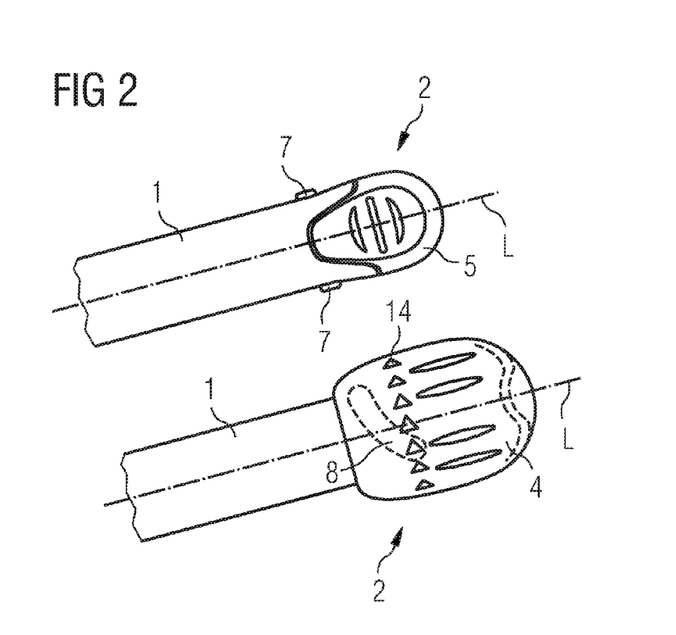
FIG. 2 shows a side view of the drug delivery device with the first and second button member.

FIG. 2 shows a proximal end 2 of an assembly of a drug delivery device in a side view in a lower and upper illustration.

The assembly of the drug delivery device comprises a longitudinal axis L and a body 1 with a proximal end 2 and a distal end (not shown). A needle unit may be located at the distal end of the body 1. Through the needle unit, a medicinal product may be dispensed out of an assembled cartridge, which is not explicitly shown.

The assembly of the drug delivery device comprises additionally a cartridge holder, inside which the cartridge is contained. The distal end of the body 1 may serve as the cartridge holder. The body 1 comprises a drive sleeve with a piston rod (not shown). The piston rod comprises a piston which is for example adapted to be in contact with a bung of the cartridge. The drive sleeve 11 and the piston rod 6 with the bearing pad 13 represent a drive assembly of the assembly of the drug delivery device for facilitating to dispensing a medicinal product.

The assembly of the drug delivery device further comprises a first button member 4 which is located at the proximal end 2 of the body 1 (see lower illustration). The first button member 4 is for example a button and is adapted to prepare, for example prime, the drug delivery device. The first button member 4 is further adapted to be detachable, in particular irreversibly detachable, from the body 1 after the drug delivery device has been prepared.

The assembly of the drug delivery device may additionally comprise a second button member 5 as depicted in the upper illustration of FIG. 2. The second button member 5 is located at the proximal end 2 of the body 1 and is for example a button. The second button member 5 is adapted to axially displace the piston rod of the drive assembly with respect to the body 1 for dispensing a single dose or multiple doses of for example a fluid medicinal product.

The second button member 5 is inaccessible as long as the preparation of the drug delivery device is uncompleted. As shown in the lower illustration in FIG. 2, the second button member 5 is fully encased by the first button member 4 to render it inaccessible as long as the first button member 4 is attached to the drug delivery device.

Alternatively, the second button member 5 is partially encased by the first button member 4. Additionally, other embodiments of the drug delivery device to render the second button member 5 inaccessible as long as the preparation of the drug delivery device is uncompleted are permissible.

In another embodiment the assembly of the drug delivery device comprises the first and second button member 4, 5 wherein the second button member 5 is rendered inaccessible as long as the preparation of the drug delivery device is uncompleted, for example by at least partially encasing it by the first button member 4. In this respect, the first button member 4 may stay attached to the assembly of the drug delivery device after the drug delivery device has been prepared, wherein a further actuation of the first button member and/or the drive assembly and/or a movement, in particular an axial movement, of the piston rod is basically blocked.

The first button member 4 may be adapted to be actuated in a predetermined movement to prepare the drug delivery device as described according to FIG. 1.

As illustrated in the upper illustration of FIG. 2 the body 1 of the assembly of the drug delivery device comprises two lugs 7. The first button member 4 of the assembly of the drug delivery device additionally comprises two guiding tracks 8. The assembly of the drug delivery device may comprise less or more than two lugs 7 and less or more than two guiding tracks 8. The number of lugs 7 basically corresponds to the number of guiding tracks 8.

The assembly of the drug delivery device may additionally comprise more or less than two lugs 7 and more or less than two guiding tracks 8 wherein the shape of different guiding track 8 may correspond to each other to allow the predetermined movement of the first button member 4. At least one lug 7 may be located on the first button member 4 and at least one lug 7 may be located on the body 1. In addition, at least one guiding track 8 may be located on the first button member 4 and at least one guiding track 8 may be located on the body 1. The number of guiding tracks 8 basically corresponds to the number of lugs 7.

A shape of the guiding track 8 along an internal surface of the first button member 4 predetermines required movements of the first button member 4 to prepare the drug delivery device. As illustrated in FIG. 2 the shape of the guiding track 8 along the internal surface of the body 1 comprises some rotational and axial movements of the first button member 4 with respect to the body 1. Alternatively, the shape of the guiding track 8 along the internal surface of the first button member 4 may additionally predetermine either some rotational or some axial movements of itself with respect to the body 1 to prepare the drug delivery device.

As shown in the lower illustration of FIG. 2, the first button member 4 comprises indicators 14. The indicators 14 indicate the required movement of the first button member 4 with respect to the body 1 according to the predetermined movement to prepare the drug delivery device. The assembly of the drug delivery device may comprise just one indicator 14. In addition, the body 1 may have at least one indicator 14.

Figure 3A:
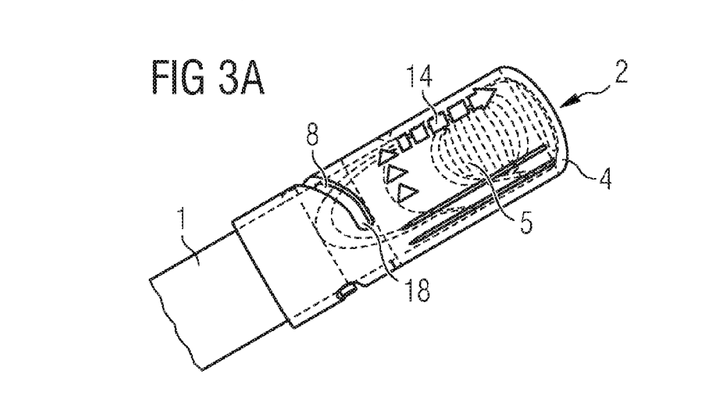
FIGS. 3a to 3c show schematical illustrations of an actuation of the first button member.
Figure 3B:
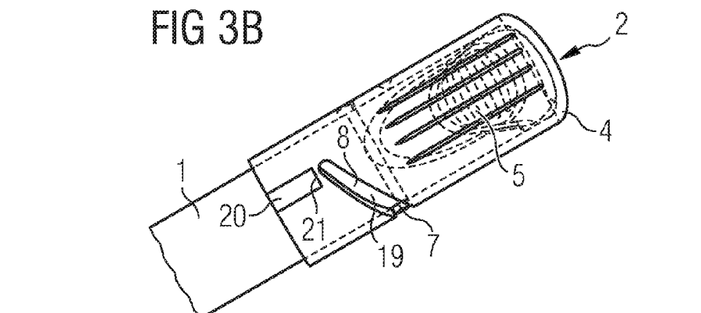
Figure 3C:
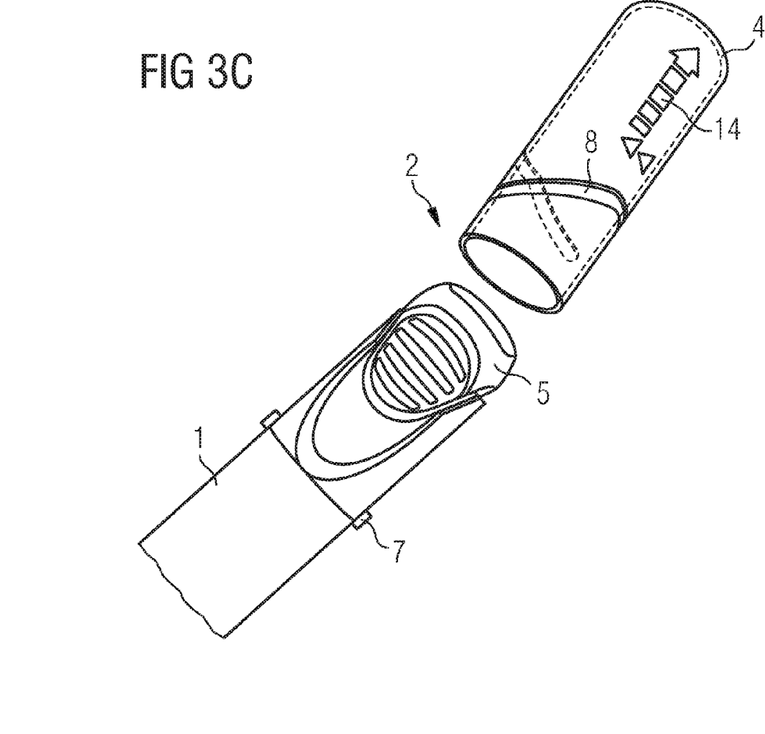

FIGS. 3a to 3c illustrate an embodiment in which the first button member 4 directly acts on the second button member 5 to prepare the drug delivery device.

FIG. 3a shows the proximal end 2 of the assembly of the drug delivery device which is in the pre-ready state. The first button member 4 fully engages the second button member 5. The second button member 5 may be in a dose-set position. In the dose-set position, the second button member 5 is moveable towards the distal end (not shown), but not moveable in a proximal direction. In the dose-set position, the second button member 5 is operable to act on the piston rod 6 to prepare or respectively dispense a single dose or multiple doses of for example a fluid medicinal product. In particular, a setting movement does not have to be performed. Rather, a dispensing movement may be commenced immediately from the dose-set position.

As illustrated in FIG. 3a the first button member 4 comprises two guiding tracks 8 in which the lugs 7 are guided in. The shape of the guiding tracks 8 along an internal surface of the first button member 4 predetermines required movements of the first button member 4 to prepare the drug delivery device. Each guiding track 8 comprises a perpendicular portion 18 which encases one of the lugs 7 in particular during the pre-ready state of the drug delivery device. The perpendicular portion 18 runs perpendicular to the longitudinal axis L of the assembly of the drug delivery device. The perpendicular portion 18 is applicable to prevent an unintentional axial movement of the first button member towards the distal end 3 of the assembly of the drug delivery device.

Each guiding track 8 additionally comprises an oblique portion 19 which directly follows upon the perpendicular portion 18. The oblique portion 19 guides the particular lug 7 in particular during the transient state of the drug delivery device. The oblique portion 19 runs obliquely with respect to the longitudinal axis L to enable an axial movement of the first button member while rotating it. The angle may be 45° with respect to the longitudinal axis L. The oblique portion 19 comprises an end that is remote from the perpendicular portion 18.

The first button member 4 may additionally comprise a removing track 20 for each lug 7. Each removing track 20 may run in parallel to the longitudinal axis L. The removing track 20 may guide the particular lug 7 during an end of the transient state. Each oblique portion 19 of the guiding track 8 may be separated from the associated removing track 20 by a detent 21. If the particular lug 7 reaches the end of the oblique portion 19 of the guiding track 8, the particular lug 7 has to get over the particular detent 21 to be guided by the particular removing track 20. The detent 21 represents a resistance against axial movement, in particular pulling, the first button member 4 in the proximal direction.

Furthermore, the first button member 4 comprises multiple indicators 14, e.g. arrows. A first set of indicators 14 indicates a first required rotational movement of the first button member 4 in the indicated rotational direction. Afterwards, a second set of indicators 14 indicates a second required axial movement of the first button member 4 in the proximal direction. Both movements may be required to prepare the drug delivery device and to make the second button member 5 accessible.

FIG. 3b shows the assembly of the drug delivery device in the transient state. That means the first button member 4 is still or already rotated in the required rotational direction indicated by the first set of indicators 14. But the first button member 4 is still attached to the body 1 of the assembly of the drug delivery device, thereby keeping the second button member 5 still inaccessible. As illustrated in FIG. 3b the first button member 4 directly acts on and contacts the second button member 5 while rotating the first button member 4, thereby urging the second button member 5 to be moved in axial direction towards the distal end (not explicitly shown).

This results in a corresponding movement of the piston rod 6 and the bearing pad 13 to prepare the drug delivery device.

FIG. 3c shows the assembly of the drug delivery device in the ready-state. That is to say, the required movements according to the first and second set of indicators 14 were completed and the first button member 4 was detached from the body 1 of the assembly of the drug delivery device. A re-attachment of the first button member 4 is prevented or at least hindered by the detents 21 (not shown in FIG. 3c). The detents 21 represent a blocking mechanism or detent feature to prevent or to at least hinder a re-attachment of the first button member 4 to the body 1 when re-attaching the first button member 4 to the body 1 and moving the first button member 4 towards the distal end 3 of the first button member 4 has been detached from the body 1.

After the first button member 4 has been detached, the second button member 5 is no longer in the dose-set position and is accessible by a user. The drug delivery device is now prepared, that means the user may set the second button member 5 in its dose-set position again and dispense a single dose or multiple doses of for example a fluid medicinal product.

Such a first button member 4 may be used with a multiplicity of drug delivery devices without changing the drive mechanism of the particular drug delivery device.

The present examples and embodiments are to be considered as illustrative and not restrictive, and the invention is not to be limited to the details given herein, but may be modified within the scope and equivalence of the appended claims.

REFERENCE NUMERALS 1 body
2 proximal end
3 distal end
4 first button member
5 second button member
6 piston rod
7 lug
8 guiding track
11 drive sleeve
13 bearing pad
14 indicator
15 snap-in area
17 movements
18 perpendicular portion of guiding track
19 oblique portion of guiding track
20 removing track
21 detent
L longitudinal axis

The invention claimed is:

1. An assembly of a drug delivery device with a longitudinal axis, comprising:
   a body comprising a proximal end and a distal end,
   a drive assembly comprising a piston rod and a drive sleeve and being at least partially arranged within the body and being adapted to facilitate dispense of a medicinal product,
   a first button member acting on the drive assembly to prepare the drug delivery device in the form of priming and/or mixing powder with a fluid and/or expelling a priming portion of the medicinal product or air during a pre-ready state and a transient state of the assembly for dispensing the medicinal product during a ready state of the assembly,
   a second button member acting on the drive assembly to dispense the medicinal product in the ready state, wherein the second button member is inaccessible as long as the preparation of the drug delivery device is uncompleted, wherein first button member encases the second button member at least partially to render it inaccessible as long as the preparation of the drug delivery device is uncompleted, wherein the first button member acting on the drive assembly to prepare the drug delivery device results in movement of a piston rod and/or the drive sleeve to prepare the drug delivery device, wherein the ready state chronologically follows the preparation during the pre-ready state and the transient state of the assembly, and wherein the first button member is adapted to be detachable From the body (i) after the preparation of the drug delivery device is completed and (ii) before dispensing of the medicinal product.

2. The assembly according to claim 1, wherein the first button member is adapted to be irreversibly detachable from the body after the preparation of the drug delivery device is completed.

3. The assembly according to claim 1, wherein the first button member is adapted to be actuated in a predetermined movement to prepare the drug delivery device.

4. The assembly according to claim 1, wherein the body comprises at least one lug and the first button member comprises at least one guiding track in which the at least one lug is guided, predetermining the movement of the first button member with respect to the body.

5. The assembly according to claim 1, wherein the first button member comprises at least one lug and the body comprises at least one guiding track in which the at least one lug is guided, predetermining the movement of the first button member with respect to the body.

6. The assembly according to claim 4, in which the at least one guiding track comprises a perpendicular portion and an oblique portion, wherein the perpendicular portion and the oblique portion are applicable to guide the at least one lug, wherein the perpendicular portion runs perpendicular to the longitudinal axis and the oblique portion runs obliquely with respect to the longitudinal axis, wherein the oblique portion directly follows up the perpendicular portion.

7. The assembly according to claim 4, in which at least one of the body or the first button member comprises at least one removing track which is applicable to guide the at least one lug wherein each removing track is associated with one oblique portion and is separated from the associated oblique portion by a detent.

8. The assembly according to claim 1, wherein the piston rod is at least partially arranged within the body and axially displaceable with respect to the body, and the drive sleeve which is arranged within the body, and axially displaceable with respect to the body, and coupled to the piston rod, and coupled to the first button member to prepare the drug delivery device.

9. The assembly according to claim 3, wherein the predetermined movement comprises some rotational movement of the first button member with respect to the body.

10. The assembly according to claim 3, wherein the predetermined movement comprises some axial displacement of the first button member with respect to the body.

11. The assembly according to claim 3, with at least one of the body or the first button member comprising at least one indicator for indicating the predetermined movement of the first button member with respect to the body.

12. The assembly according to claim 1, adapted to prevent an actuation of the first button member after the preparation the drug delivery device has been completed.

13. The assembly according to claim 1, adapted to prevent the actuation of the first button member in a reverse predetermined movement after the preparation the drug delivery device has been completed.

14. The assembly according to claim 1, wherein a predetermined dose of a fluid medicinal product is dispensed by actuating a second button member.

15. An assembly of a drug delivery device with a longitudinal axis, the assembly comprising:

a body comprising a proximal end and a distal end;

a drive assembly comprising a piston rod and a drive sleeve and being at least partially arranged within the body and being adapted to facilitate dispense of a dose of medicinal product;

a first button member configured to act on the drive assembly to prime the drug delivery device during a pre-ready state and a transient state of the assembly for dispensing the medicinal product during a ready state of the assembly, a second button member acting on the drive assembly to dispense the medicinal product in the ready state, wherein the second button member is inaccessible as long as the preparation of the drug delivery device is uncompleted, wherein first button member encases the second button member at least partially to render it inaccessible as long as the preparation of the drug delivery device is uncompleted, wherein the ready state chronologically follows the priming during the pre-ready state and the transient state of the assembly, and wherein the first button member is adapted to be detachable from the body (i) after the priming of the drug delivery device is completed and (ii) before dispensing of the dose of medicinal product.

* * * * *